(12) United States Patent
Lin et al.

(10) Patent No.: US 8,279,436 B2
(45) Date of Patent: Oct. 2, 2012

(54) TRACE DETECTION DEVICE OF BIOLOGICAL AND CHEMICAL ANALYTES AND DETECTION METHOD APPLYING THE SAME

(75) Inventors: Ding-Zheng Lin, Taipei (TW); Tien-Li Chang, Kaohsiung (TW); Jen-You Chu, Changhua County (TW); Yi-Ping Chen, Kaohsiung County (TW); Pei-Chen Chuang, Taipei (TW); Bean-Jon Li, Hsinchu (TW); Chiung-Hui Huang, Tainan County (TW); Jyi-Tyan Yeh, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 288 days.

(21) Appl. No.: 12/720,605

(22) Filed: Mar. 9, 2010

(65) Prior Publication Data

US 2011/0109902 A1     May 12, 2011

(30) Foreign Application Priority Data

Nov. 6, 2009    (TW) ............................ 98137759 A

(51) Int. Cl.
*G01J 3/44*      (2006.01)
*G01N 21/55*     (2006.01)

(52) U.S. Cl. ............................ 356/301; 356/445; 438/14
(58) Field of Classification Search .......... 356/432–440, 356/301, 445–448; 438/14–16
See application file for complete search history.

(56) References Cited

U.S. PATENT DOCUMENTS

| | | | |
|---|---|---|---|
| 6,985,223 B2 * | 1/2006 | Drachev et al. | 356/301 |
| 7,242,470 B2 * | 7/2007 | Cullum et al. | 356/301 |
| 7,321,422 B2 | 1/2008 | Li et al. | |
| 7,397,558 B2 | 7/2008 | Kamins et al. | |
| 7,460,224 B2 | 12/2008 | Wang et al. | |
| 7,474,397 B2 * | 1/2009 | Wang et al. | 356/301 |
| 2002/0182716 A1 * | 12/2002 | Weisbuch et al. | 435/287.2 |
| 2004/0180379 A1 | 9/2004 | Van Duyne et al. | |
| 2005/0123442 A1 * | 6/2005 | Gu et al. | 422/57 |
| 2006/0119853 A1 | 6/2006 | Baumberg et al. | |
| 2007/0285657 A1 | 12/2007 | Wang et al. | |
| 2009/0128822 A1 * | 5/2009 | Yamamichi et al. | 356/445 |
| 2011/0317160 A1 * | 12/2011 | Li et al. | 356/301 |

* cited by examiner

*Primary Examiner* — Hoa Pham

(57) ABSTRACT

Disclosed is a trace detection device of a biological and chemical analyte, including a metal substrate, a periodic metal nanostructure on the metallic substrate, a dielectric layer on the periodic metal nanostructure, and a continuous metal film on the dielectric layer. Tuning the thickness of the dielectric layer and/or the continuous metal film to meet the laser wavelength can shift the absorption peak wavelength of the sensor, thereby further enhancing the Raman signals of the analyte molecules.

19 Claims, 7 Drawing Sheets

TRACE DETECTION DEVICE OF BIOLOGICAL AND CHEMICAL ANALYTES AND DETECTION METHOD APPLYING THE SAME

CROSS REFERENCE TO RELATED APPLICATIONS

This Application claims priority of Taiwan Patent Application No. 098137759, filed on Nov. 6, 2009, the entirety of which is incorporated by reference herein.

BACKGROUND OF THE INVENTION

1. Field of the Invention

The present invention relates to trace detection of chemical and biological analyte, and in particular relates to the substrate and structure thereof.

2. Description of the Related Art

There are several poisonous chemical pollutants in the environment, and these pollutants have different detection standards, e.g. Amphetamine series (500 ppb), Cannabis metabolite (50 ppb), Paraquat (10 ppb), EPN (0.5 ppb), benzene (5.0 ppb), Clenbuterol (2.0 ppb), Malachite Green (2.0 ppb), nitrofuran (1.0 ppb), chloromycetin (0.3 ppb), and the likes. Only a few pollutants can be detected by immunization, most pollutants are quantitatively detected using mass spectrometry. Immunization is difficult to quantitatively analyze, and it needs further analysis such as mass spectrometry to improve detection reliability. However, mass spectrometry is expensive and time consuming, thereby limiting its timeliness and popularity. Therefore, those skilled in the art have spent significant effort to develop a highly sensitive, rapid, and low cost trace detection device to analyze biological and chemical analytes.

Raman scattering spectrum belongs to molecular vibration spectrum, and its full width half maximum (FWHM) width is far less than that of the fluorescence spectrum. As such, the Raman spectrum has the fingerprint specificity to express the molecular structure. However, the Raman scattering intensity is very weak. For example, about $10^6$ to $10^8$ incident photons make only 1 Raman scattering of inelastic collision, such that the trace detection based on the Raman scattering is difficult. The surface plasmon (in abbreviate SP) may resonant to form an ultra high electric field by the interaction of the metal nanostructure and the incident electromagnetic wave, thereby largely enhancing the Raman scattering. The described phenomenon is a so-called surface enhanced Raman scattering (in abbreviate SERS). It makes trace diction based on Raman scattering possible.

In U.S. Pat. No. 7,321,422 and U.S. Publication No. 2007/0285657, a periodic structure is formed on the substrate. However, the periodic structure has no continuous metal film thereon; it will limit its ability to adsorb significant amounts of magnetic molecules or positive/negative ions.

In U.S. Pat. No. 7,242,470, a nanostructure is formed on a substrate surface. However, this nanostructure is not periodic and its signal has low uniformity and reproducibility.

In U.S. Publication No. 2006/0119853, a commercial substrate is provided. The photon lattice structure 201, made of metal, a dielectric layer and a Bragg reflector 209 is adopted to enhance the Raman signals of the analyte 211 approaching the substrate. However, the surface structure of the silicon substrate is formed by physical etching or chemical etching, it is expensive and time costly.

Accordingly, a novel design of the detection device is still called for in order to solve the conventional problems.

BRIEF SUMMARY OF THE INVENTION

The invention provides a trace detection device for biological and chemical analytes, comprising a metal substrate; a periodic metal nanostructure on the metal substrate; a dielectric layer on the periodic metal nanostructure; and a continuous metal film on the dielectric layer.

The invention also provides a trace detection method for biological and chemical analytes which comprises providing a trace detection device of biological and chemical analyte as claimed in claim 1 to adsorb an analyte molecule; and providing a laser excitation light to the analyte to form a Raman scattering signal.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The commercialization of the trace detection device for biological and chemical analytes depends on several conditions: high sensitivity, high stability, excellent uniformity, quantitatively analysis, easy to use and low cost. To accomplish the described conditions, the periodic meal nano structure having a high surface electrical field is selected to meet the described requirements, especially for its low cost material and simple process. The nanostructure of the invention can enhance the Raman signal; it is produced by simple nano processes such as nanoimprint and nano electroforming. Furthermore, the thickness of the continuous metal film and dielectric layer can be changed to red or blue shift the surface plasmon resonance wavelength of the device. The device of the invention can be applied to detect the trace chemical or biological analytes, e.g. Malachite green of less than 1 ppb, wherein the local stability variation of the analysis is less than 5%, and the signal intensity is stable versus time.

Figure 1A:
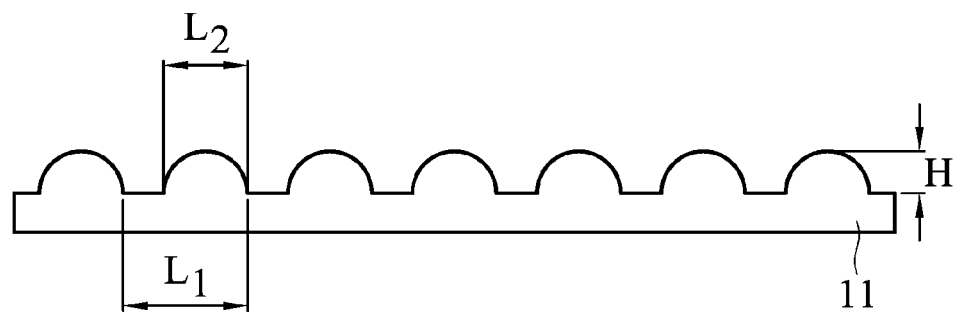
FIGS. 1A-1D are cross sections showing the processes of forming the trace detection device of chemical and biological analyte.

As shown in FIG. 1A, the periodic metal nanostructure 11 is first formed by nanoimprint or nano electroforming. See Microelectronic Engineering 85, 1608-1612 (2008) and Microelectronic Engineering 86, 874-877 (2009). The described metal nanostructure 11 includes nickel, aluminum, gold, silver, copper, or alloys thereof. Although the nanostructure in FIG. 1A has a semi-sphere shape, it can be other shapes such as a column, sine wave, rectangle, and the likes if necessary. In one embodiment, the periodic metal nanostructure 11 has a period $L_1$ of 50 nm to 1000 nm. If the period $L_1$ is too short, the process thereof is difficult or even impossible. If the period $L_1$ is too long, it cannot match the following incident laser wavelength for detection. In one embodiment, the periodic metal nanostructure 11 has a width to period ratio of ($L_2/L_1$) of 1:10 to 9:10. If the ratio $L_2/L_1$ is too large, the transfer process of the imprint nanostructure is difficult. If the $L_2/L_1$ is too low, it cannot efficiently improve the plasmon resonance on the device surface and the Raman signal of the analyte. In one embodiment, the periodic metal nanostructure 11 has an aspect ratio $H/L_2$ of 0.5 to 5. If the aspect ratio $H/L_2$ is too low, the nanostructure is too flat to obtain the effect of the surface plasmon resonance. If the aspect ratio $H/L_2$ is too high, the process difficulty of the nanoimprint or nano electroforming will be largely increased.

Figure 1B:
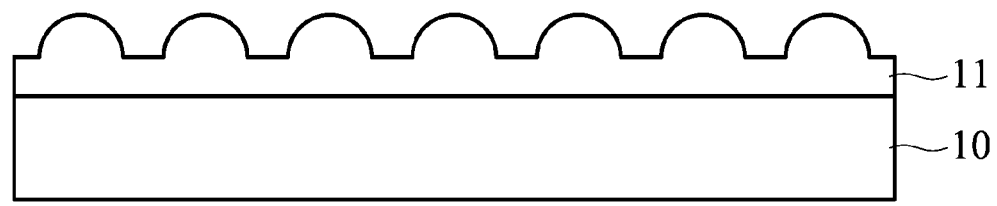

AS shown in FIG. 1B, the periodic metal nanostructure 11 is following formed on a metal substrate 10 by electroless plating or nanoimprint. The metal substrate 11 can be nickel, aluminum, gold, silver, copper, or alloys thereof. In another embodiment, the periodic metal nanostructure is directly formed on the substrate 10 by imprint, electroforming, or the likes. Whichever method is selected, the periodic metal nanostructure 11 and the metal substrate can be composed of the same or different materials. If a two-stepwise process is selected to form the structure as shown in FIG. 1B, the different metals having different factors can be selected to meet the different requirements of separate elements. For example, the periodic metal nanostructure 11 needs thinner thickness to benefit the nanoimprint and electroless plating process. Moreover, the periodic metal nanostructure should be an expensive metal to rapidly conduct heat, thereby preventing heat from accumulating on the local surface, which can break its structure. On the other hand, the metal substrate 10 may adopt thicker thickness to increase the product's mechanical strength. The metal substrate 10 can be composed of relatively inexpensive metal, having lower thermal conductivity, to reduce the cost.

Figure 1C:
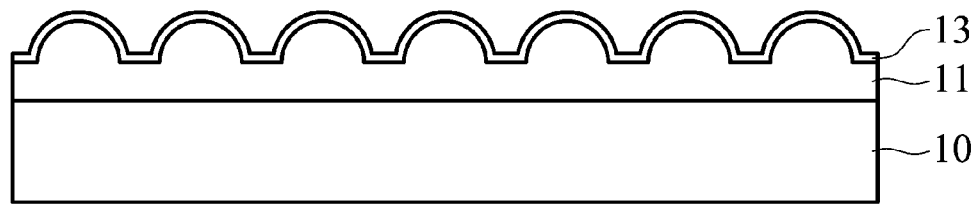

As shown in FIG. 1C, the dielectric layer 13 is then conformally formed on the periodic metal nanostructure 11. The dielectric layer 13 can be a material having a refractive index (n) of 1.5 to 4, such as silicon dioxide (n=1.5), aluminum oxide (n=1.6), silicon nitride (n=2), titanium dioxide (n=2.9), silicon (n=4), or the likes. The dielectric layer 13 has a thickness of 1 nm to 1000 nm. If the dielectric layer 13 is too thick, the periodic metal nanostructure will be filled to flat and the effect of the surface plasmon resonance will diminish. If the dielectric layer 13 is too thin, the effect of the surface plasmon resonance will also be degraded.

Figure 1D:
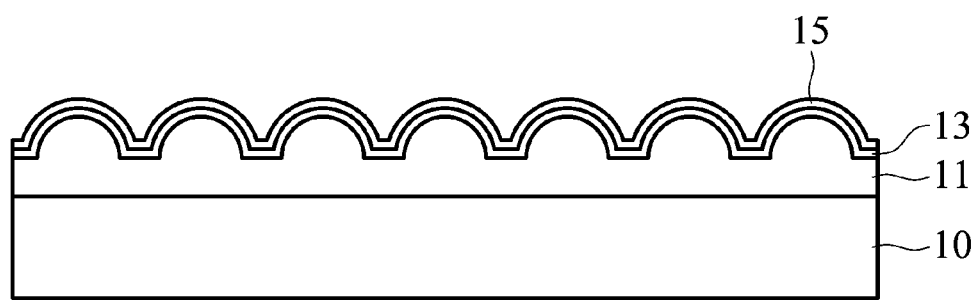

As shown in FIG. 1D, a continuous metal film 15 is conformably formed on the dielectric layer 13, such that the trace detection device of chemical and biological analyte is obtained. The continuous metal film includes noble metal such as gold, silver, or platinum, transition metals such as iron, cobalt, or nickel, or alloys thereof. In one embodiment, the continuous metal film 15 has a thickness of 1 nm to 200 nm. If the continuous metal film 15 is too thick, it is far thicker than the metal skin depth, and the extra metal thickness has no contribution to the surface plasmon resonance. Moreover, the overly thick continuous metal film will reduce the aspect ratio ($H/L_2$) of the periodic metal nanostructure. If the continuous metal film is too thin, it will be difficult to form a continuous metal film with uniform thickness. The continuous metal film 15 is one important feature of the invention because the electrical or magnetic fields can be applied to the continuous metal film 15 to increase the adsorption capacity of the analyte, thus, trace detection capability is increased. If the metal film is a discontinuous structure, the electrical field cannot be applied to reach the described effect.

The trace detection device as shown in FIG. 1D can be utilized to detect the chemical and biological analytes in gas or liquid samples. In one embodiment, the analyte in a gas sample has a concentration of 100 ppm to 1 ppb, and the analyte in a liquid sample such as in water or organic solvent has a concentration of 100 ppm to 0.1 ppb. In the invention, the detection limit of the Malachite Green in aqueous solution is extra low as $10^{-10}$M (about 0.1 ppb).

Because the elements of the detection device in the invention are composed of acid/base/solvent resistant materials, the solvent of the liquid sample can be water or organic solvent having a pH of 2 to 12. In addition, both the metal substrate 10 and the periodic metal nanostructure 11 are composed of thermally conductive metal, this may prevent heat from accumulating on the local surface and breaking the periodic metal nanostructure, thereby improving the device lifetime and performance.

After the analyte in the sample is adsorbed on the continuous metal film 15 of the device surface, the device is exposed to a laser having a wavelength between 400 nm to 1200 nm and the Raman scattering signal of the analyte is thus produced. The laser may include solid state laser having a wavelength of 355 nm, 532 nm, or 1064 nm, a gas laser having a wavelength of 488 nm, 514 nm, or 633 nm, a semiconductor laser having a wavelength of 405 nm, 532 nm, 635 nm, 670 nm, 780 nm, or 1064 nm, and the likes. Because the continuous metal film 15 has periodic nanostructure, its surface plasmon resonance effect may enhance the Raman signal. In addition, the surface plasmon resonance wavelength can be tuned to be coincident with the incident laser by changing the thickness of the dielectric layer 13 and the continuous metal film 15, such that the Raman signal intensity of the analyte is further increased. Reducing the thickness of the dielectric layer 13 and/or increasing the thickness of the continuous metal film 15 will blue shift (shortening the wavelength) the surface plasmon resonance wavelength. Alternatively, increasing the thickness of the dielectric layer 13 and/or reducing the thickness of the continuous metal film 15 will red shift (lengthening the wavelength) the surface plasmon resonance wavelength. In addition, the refractive index of the medium in the sample also influences the surface plasmon resonance wavelength of the device. For example, increasing the refractive index of the medium of the sample containing the analyte (e.g. from air to water), will increase the surface plasmon resonance wavelength of the device to become red shifted (lengthened).

Compared to the conventional arts, the trace detection device of the chemical and biological analyte has several advantages which are listed below. First, the substrate of the device is an acid/base/solvent resistant metal and is widely applied in several mediums. Second, the excellent thermal conductivity of the substrate may solve problems associated with the breaking of the periodic nanostructure which is caused by heat produced from the laser. This advantage will help increase the lifetime of the device. Third, the surface plasmon resonance wavelength of the device can be tuned to be coincident with the incident laser wavelength by changing the thickness of the dielectric layer and the continuous metal film, such that the Raman signal is enhanced. Therefore, a similar periodic nanostructure can be adopted without modifying its factors for different laser wavelength. Finally, the continuous metal film can be applied to an electrical field and/or a magnetic field to increase the adsorption capacity of the analyte for enhancing the Raman signal intensity.

EXAMPLES

Example 1

Figure 2:
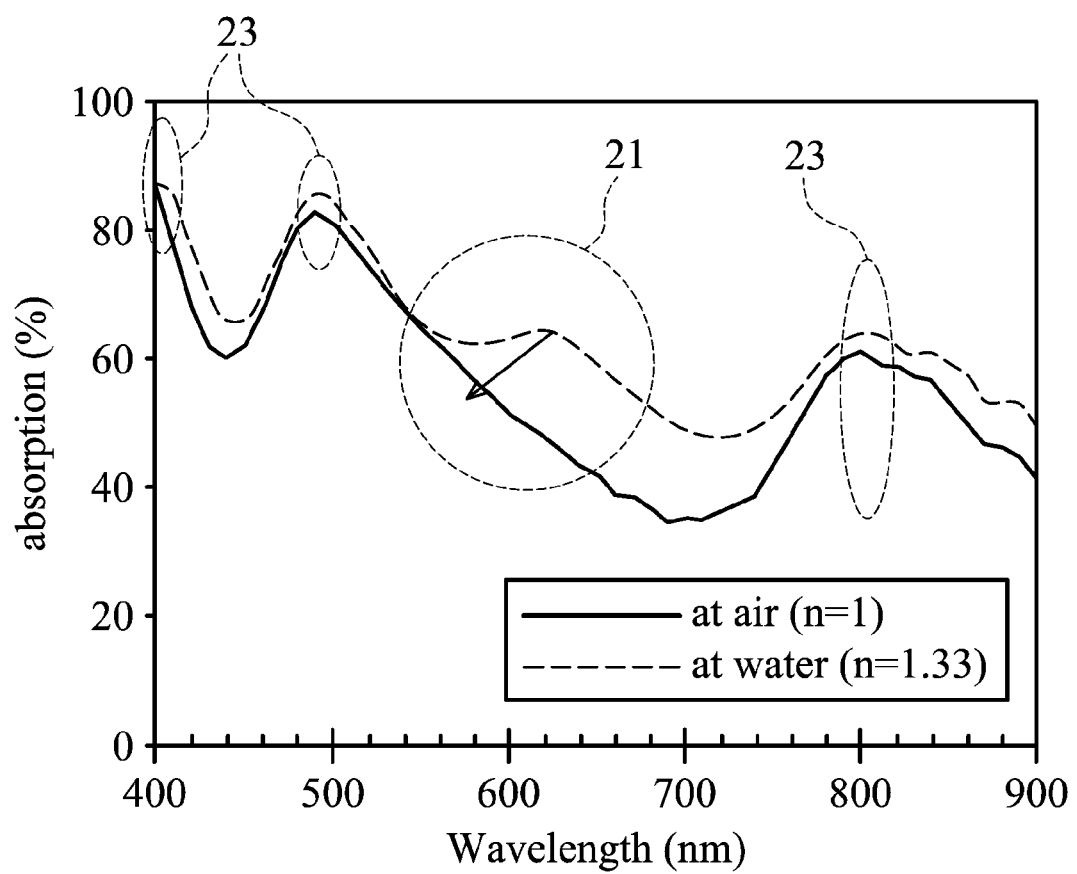
FIG. 2 is a schematic view showing the absorption spectra comparison of the trace detection device in different mediums in one embodiment of the invention.

A periodic nickel nanostructure was formed by nanoimprint, and then transformed on a nickel substrate by electroless plating. The periodic nickel nanostructure had a shape of a sine wave, a period ($L_1$) of 300 nm, a width ($L_2$) of 150 nm, and a height (H) of 150 nm, wherein the aspect ratio (H/$L_2$) is 1. 400 nm of silicon dioxide layer was then conformably formed on the periodic nickel nano structure by chemical vapor deposition, and 20 nm of continuous silver film was then conformably formed on the silicon dioxide layer by sputtering. As such, the continuous silver film was formed on the nickel substrate, and the silicon dioxide layer is disposed therebetween. The described device was charged in different mediums such as air and water to measure its absorption ratio versus different wavelengths. As shown in the dotted circle 21 of FIG. 2, when the device was moved from water having higher refractive index to air having lower refractive index, its surface plasmon resonance absorption peak wavelength was blue shifted due to refractive index decrease of the medium. In addition, the dotted circles 23 in FIG. 2 showed the absorption peaks caused by thin film interference of the metal-dielectric-metal sandwich structure.

Comparative Example 1

Figure 3:
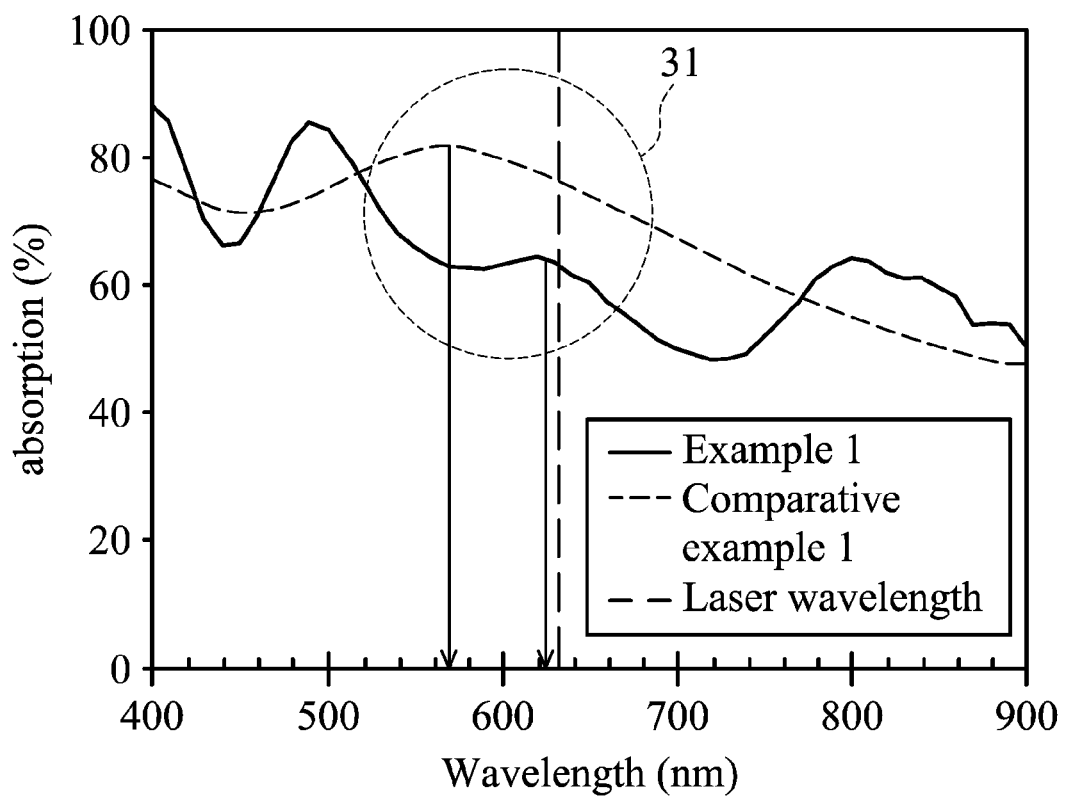
FIG. 3 is a schematic view showing the absorption spectra comparison of the trace detection device having the dielectric layer or the trace detection device without the dielectric layer in water in one embodiment of the invention.

Similar to Example 1, the difference was that the continuous silver film was directly formed on the periodic nickel nanostructure without the silicon dioxide layer therebetween in Comparative Example 1. The devices of Example 1 and Comparative Example 1 were charged in water to measure their absorption capability versus different wavelengths. As shown in the dotted circle 31 in FIG. 3, the absorption peak wavelength of the device having the silicon dioxide layer in Example 1 was red shifted compared to the device in Comparative Example 1. Because the absorption peak wavelength of the device in Example 1 was close to the incident laser wavelength (633 nm), the Raman signal of the analyte molecule would be enhanced.

As described as above, the absorption peak wavelength of the device could be tuned to be coincident with the incident laser wavelength by changing the dielectric layer thickness on the same periodic nanostructure.

Comparative Example 2

Figure 4:
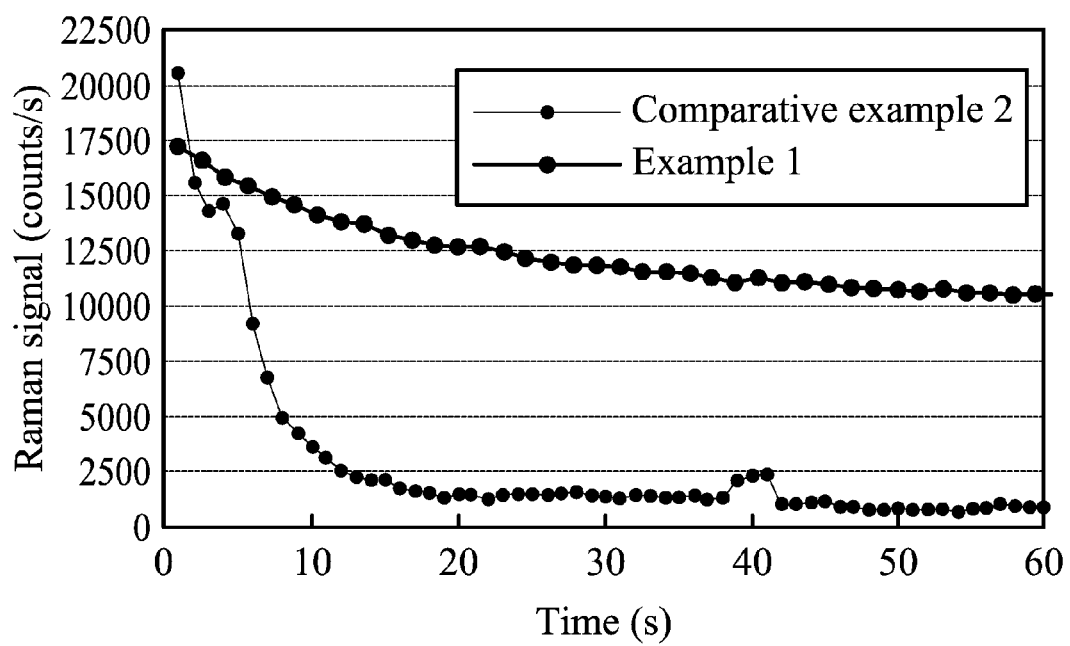
FIG. 4 is a schematic view showing the Raman signal stability versus time of the trace detection devices having metal or plastic substrates in one embodiment of the invention.
Figure 5:
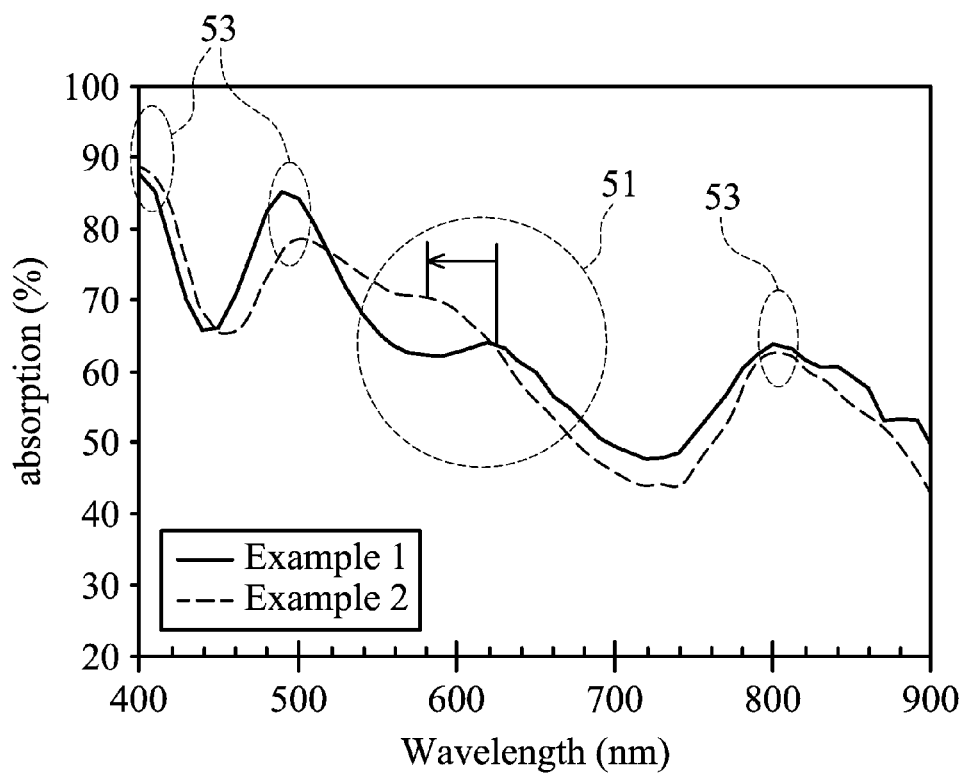
FIG. 5 is a schematic view showing the absorption spectra comparison of the trace detection devices having continuous metal films of different thickness in water in one embodiment of the invention.

Similar to Comparative Example 1, the difference was that the substrate and the periodic nanostructure material being replaced from nickel to poly(ethylene terephthalate) (in abbreviate PET) in Comparative Example 2, and the other periodic nanostructure factors such as period and aspect ratio were same. The dye (Rhodamine 6G) having a character absorption peak wavelength of 1365 $cm^{-1}$ was chosen as the analyte. The devices of Example 1 and Comparative Example 2 were put in the analyte aqueous solution to measure their signal intensities versus laser exposing time (0 to 60 seconds). As shown in FIG. 4, the signal intensity of the device in Example 1 was stable after being exposed to the laser for 60 seconds. On the other hand, the signal intensity of the device in Comparative Example 2 largely decayed after being exposed to the laser for less than 10 seconds. After observing the results, the surface of the device in Comparative Example 2 generated bubbles after being exposed to the laser. Accordingly, the device of the invention might efficiently dissipate heat to avoid breaking the periodic nanostructure on the device surface, such that the signal remains stable. The substrate of the device in Comparative Example 2 was PET with lower thermal conductivity and resistance. The nanostructure on the device surface was easily broken and inactive after being exposed to the laser.

Example 2

Similar to Example 1, the difference was that the continuous silver film thickness thickened from 20 nm to 25 nm in Example 2, other periodic nickel nanostructure factors and the silicon dioxide layer thickness were same. The devices of Examples 1 and 2 were charged in water to measure their absorptions versus different wavelength. As shown in the dotted circle 51 in FIG. 3, the surface plasmon resonance absorption peak wavelength of the device having thicker continuous silver film in Example 2 was blue shifted compared to the device in Example 1. In addition, the dotted circles 53 showed the absorption peaks caused by thin film interference of the metal-dielectric-metal sandwich structure.

As described above, the absorption peak wavelength of the device could be tuned to coincide with the incident laser wavelength by changing the continuous metal film thickness on the same periodic nanostructure.

Example 3

Figure 6:
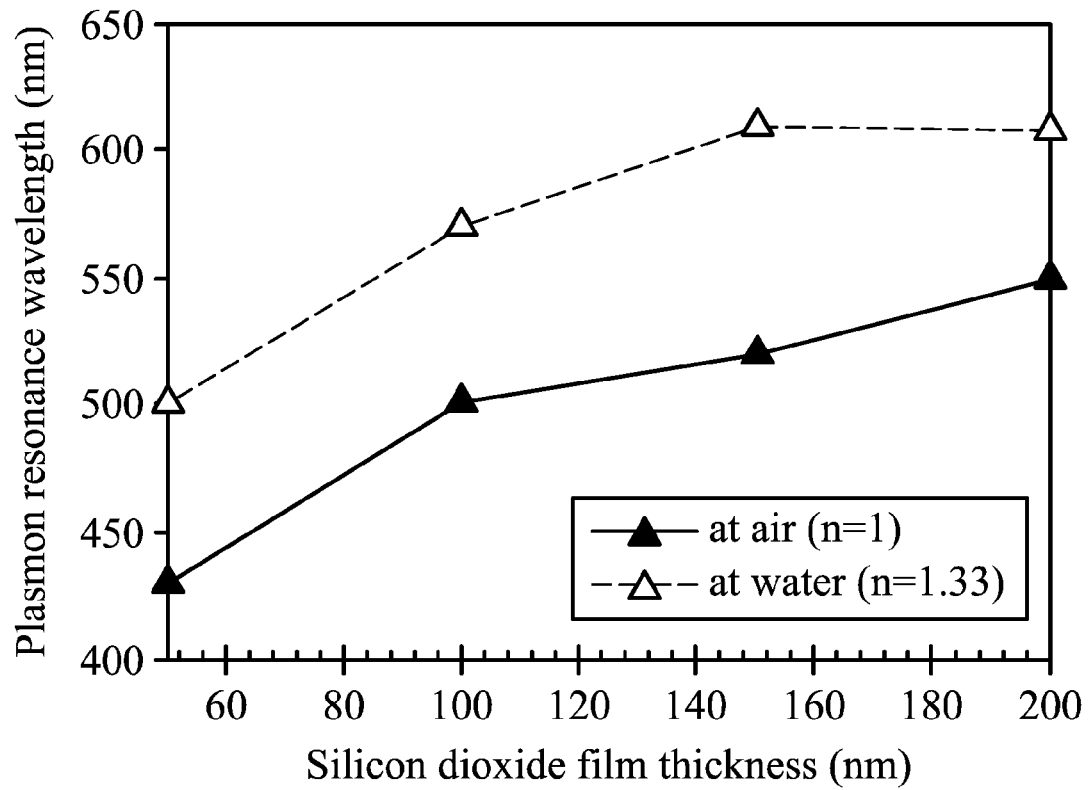
FIG. 6 is a schematic view showing the wavelength of surface Plasmon resonance peak of the trace detection devices having dielectric layers of different thickness in water or in air in one embodiment of the invention.

Four periodic nickel nanostructures as described in Example 1 were provided, and 50 nm, 100 nm, 150 nm, and 200 nm of silicon dioxide layers were conformably formed on the different periodic nickel nanostructures by chemical vapor deposition, respectively. Subsequently, 25 nm continuous silver films are conformably formed on the silicon dioxide layers, respectively by sputtering, such that the devices having the periodic nanostructures, the continuous silver films, and the silicon dioxide layer having different thickness therebetween were obtained. The devices of Example 3 were charged in different mediums such as air and water to measure their absorption peaks due to surface plasmon resonance. As shown in FIG. 6, the surface plasmon resonance absorption peak wavelength of the devices was red shifted by thickening the dielectric layer, it meant that the surface plasmon resonance absorption peak wavelength could be tuned by changing the dielectric layer thickness. In addition, the surface plasmon resonance absorption wavelength of the devices was blue shifted due to the refractive index decrease of the medium (e.g. from water to air).

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A trace detection device of a biological and chemical analyte, comprising:
    a metal substrate;
    a periodic metal nanostructure formed on the metal substrate;
    a dielectric layer conformally formed on the periodic metal nanostructure; and
    a continuous metal film conformally formed on the dielectric layer.

2. The trace detection device of the biological and chemical analyte as claimed in claim 1, wherein the metal substrate and the periodic metal nanostructure are composed of same materials or different materials.

3. The trace detection device of the biological and chemical analyte as claimed in claim 1, wherein the metal substrate comprises nickel, aluminum, gold, silver, copper, or alloys thereof.

4. The trace detection device of the biological and chemical analyte as claimed in claim 1, wherein the periodic metal nanostructure comprises nickel, aluminum, gold, silver, copper, or alloys thereof.

5. The trace detection device of the biological and chemical analyte as claimed in claim 1, wherein the periodic metal nanostructure has a shape of semi-sphere, column, sine wave, or rectangle.

6. The trace detection device of the biological and chemical analyte as claimed in claim 1, wherein the periodic metal nanostructure has a period of 50 nm to 1000 nm.

7. The trace detection device of the biological and chemical analyte as claimed in claim 1, wherein the periodic metal nanostructure has a width to period ratio from 0.1 to 0.9.

8. The trace detection device of the biological and chemical analyte as claimed in claim 1, wherein the periodic metal nanostructure has a height to width ratio from 0.5 to 5.

9. The trace detection device of the biological and chemical analyte as claimed in claim 1, wherein the dielectric layer has a thickness of 1 nm to 1000 nm.

10. The trace detection device of the biological and chemical analyte as claimed in claim 1, wherein the dielectric layer comprises a material having a refractive index of 1.3 to 4.

11. The trace detection device of the biological and chemical analyte as claimed in claim 1, wherein the dielectric layer comprises silicon dioxide having a refractive index of 1.5, aluminum oxide having a refractive index of 1.6, silicon nitride having a refractive index of 2, titanium dioxide having a refractive index of 2.9, or silicon having a refractive index of 4.

12. The trace detection device of the biological and chemical analyte as claimed in claim 1, wherein the continuous metal film has a thickness of 1 nm to 1000 nm.

13. The trace detection device of the biological and chemical analyte as claimed in claim 1, wherein the continuous metal film uses gold, silver, platinum, iron, cobalt, nickel, or alloys thereof.

14. A trace detection method of a biological and chemical analyte, comprising:
    providing the trace detection device of the biological and chemical analyte as claimed in claim 1 to adsorb the analyte molecule; and
    providing a laser excitation light to the analyte to form a Raman scattering signal.

15. The method as claimed in claim 14, further comprising applying an electrical field and/or a magnetic field to the continuous film to enhance the adsorption of the analyte molecule to the trace detection device of the biological and chemical analyte.

16. The method as claimed in claim 14, wherein the analyte molecule is charged in a medium of pH 2 to pH 12.

17. The method as claimed in claim 14, wherein the analyte molecule is charged in a medium, the medium being water or organic solvent, and the analyte concentration in the medium is 100 ppm to 0.1 ppb.

18. The method as claimed in claim 14, wherein the analyte molecule is charged in a medium, the medium is air, and the analyte concentration in the medium is 100 ppm to 1 ppb.

19. The method as claimed in claim 14, further comprising tuning the thickness of the continuous metal film or the dielectric layer to enhance the Raman scattering signal strength.

* * * * *